US00PP17375P3

(12) United States Plant Patent
Danziger

(10) Patent No.: US PP17,375 P3
(45) Date of Patent: Jan. 23, 2007

(54) **NEW GUINEA *IMPATIENS* PLANT NAMED 'DANHARDAROR'**

(50) Latin Name: *Impatiens hawkeri*
Varietal Denomination: Danhardaror

(75) Inventor: Gabriel Danziger, Moshav Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 11 days.

(21) Appl. No.: 11/122,020

(22) Filed: May 5, 2005

(65) Prior Publication Data

US 2006/0253949 P1 Nov. 9, 2006

(51) Int. Cl.
*A01H 5/00* (2006.01)

(52) U.S. Cl. ..... Plt./318

(58) Field of Classification Search ..... Plt./318
See application file for complete search history.

*Primary Examiner*—Kent Bell
(74) *Attorney, Agent, or Firm*—Foley & Lardner LLP

(57) ABSTRACT

A new and distinct New Guinea *Impatiens* plant named 'Danhardor' characterized by having large, round, dark lavender flowers, containing a red eye in the center; green leaves; highly branched; and a compact, round growth habit.

2 Drawing Sheets

Botanical designation: *Impatiens hawkeri.*
Variety denomination: 'Danhardaror'.

BACKGROUND OF THE INVENTION

The present invention relates to a new and distinct cultivar of New Guinea *Impatiens* plant, botanically known as *Impatiens hawkeri,* hereinafter referred to by the cultivar name 'Danhardaror'. The genus of *Impatiens* belongs to the Balsaminacea family.

The new *Impatiens* cultivar is a product of a planned breeding program conducted by the Inventor, Gabriel Danziger, in Moshav Mishmar Hashiva, Israel. The objective of the breeding program is to develop a new *Impatiens* variety with large, round, dark lavender flowers containing a red eye in the center, green leaves and a compact growth habit.

'Danhardaror' originated from a cross made in a controlled breeding program by the Inventor in 2002 in Moshav Mishmar Hashiva, Israel. The female or seed parent is the *Impatiens hawkeri* cultivar designated 'A-616' (unpatented) and is characterized by having round, lavender flowers and a compact growth habit. The male parent is the *Impatiens hawkeri* cultivar designated 'H-313' (unpatented) and is characterized by having large, round flowers in a salmon color and a compact growth habit. 'Danhardaror' was discovered and selected by the Inventor in June of 2002 as a flowering plant within the progeny of the stated cross in a controlled environment in Moshav Mishmar Hashiva, Israel.

Asexual reproduction of the new cultivar was performed by leaf cuttings. The cuttings are from an apical bud that has no more than two expanded leaves and three to four immature leaves present. Asexual reproduction of 'Danhardaror' was first performed in December of 2001 in Moshav Mishmar Hashiva, Israel, and has demonstrated that the combination of characteristics as herein disclosed for the new cultivar are firmly fixed and retained through successive generations of asexual reproduction. The new cultivar reproduces true-to-type.

BRIEF DESCRIPTION OF THE INVENTION

The following traits have been repeatedly observed and are determined to be unique characteristics of 'Danhardaror' which in combination distinguish this *Impatiens* as a new and distinct cultivar:

1. Large, round flowers;
2. Dark lavender flower color;
3. Green leaves;
4. Highly branched; and
5. Compact and round growth habit.

Plants of the new *Impatiens* cultivar 'Danhardaror' differ from plants of the parents, 'A-616' (unpatented) and 'H-313' (unpatented), in the following characteristics described in Table 1:

TABLE 1

| Trait | New Cultivar 'Danhardaror' | Female Parent 'A-616' (unpatented) | Male Parent 'H-313' (unpatented) |
|---|---|---|---|
| Color of fully opened petals (upper surface): | Purple group: RHS N78B | Purple group: RHS N78C | Red group: RHS 43D |
| Leaf size | Length: 12 cm Width: 2.5 cm | Length: 10 cm Width: 3 cm | Length: 11 cm Width: 3.5 cm |
| Plant height | 18 cm | 19 cm | 18 cm |

Of the many commercial cultivars known to the present Inventor, the most similar in comparison to the new *Impatiens* cultivar 'Danhardaror' is the *Impatiens* cultivar 'Danhardalil', described in co-pending U.S. Plant patent application Ser. No. 10/846,635. In side-by-side comparisons conducted in Moshav Mishmar Hashiva, Israel, plants of 'Danhardaror' differed from plants of 'Danhardalil' in the following characteristics described in Table 2:

TABLE 2

| Trait | New Cultivar 'Danhardaror' | Comparison Cultivar 'Danhardalil' |
|---|---|---|
| Size of flower | 7 cm | 8 cm |
| Plant height | 18 cm | 15 cm |
| Flower center color | Small, red-purple eye. Red-Purple Group: RHS 67B | Small, white eye. White Group: RHS 155D |

BRIEF DESCRIPTION OF THE DRAWINGS

The accompanying colored photographs illustrate the overall appearance of the new *Impatiens* cultivar 'Danhardaror' showing the colors as true as is reasonably possible with colored reproductions of this type. Colors in the photographs may differ slightly from the color values cited in the detailed botanical description which accurately describe the color of the 'Danhardaror'.

The first photograph shows a top perspective view of a typical flowering plant of 'Danhardaror' in a 12 to 13 c.m. pot, at 15 weeks of age.

The second photograph shows a close-up view of the typical flowers, buds and leaves of 'Danhardaror' at 15 weeks of age.

DETAILED BOTANICAL DESCRIPTION

'Danhardaror' has not been observed under all possible environmental conditions. The phenotype of the new cultivar may vary with variations in environment such as temperature, light intensity, and daylength, without any change in the genotype of the plant.

The aforementioned photographs, together with the following observations, measurements and values describe plants of the new *Impatiens* cultivar 'Danhardaror' as grown in a greenhouse in Moshav Mishmar Hashiva, Israel, under conditions which closely approximate those generally used in commercial practice. Plants of 'Danhardaror' were grown in a greenhouse with day temperatures ranging from 25° C. to 30° C. at night temperatures ranging from 18° C. to 25° C. Plants of 'Danhardaror' were fertilized up to a level of 100 ppm N, 35 ppm P and 120 ppm K.

Color references are made with The Royal Horticultural Society Colour Chart (R.H.S.), 2001 edition, except where general colors of ordinary significance are used. Color values were taken under daylight conditions at approximately 12 noon in Moshav Mishmar Hashiva, Israel. The photographs and descriptions were taken during the winter when outdoor day temperatures ranged from 15° C. to 25° C. and outdoor night temperatures ranged from 10° C. to 15° C. The age of the plants described is 15 weeks.

Classification:

*Botanical.*—*Impatiens hawkeri.*

Parentage:

*Female or seed parent.*—*Impatiens hawkeri* cultivar designated 'A-616' (unpatented).

*Male parent.*—*Impatiens hawkeri* cultivar designated 'H-313' (unpatented).

Propagation:

*Type.*—Leaf cutting.

*Time and temperature to initiate roots.*—Summer: 7 to 10 days at 25° C. Winter: 10 to 15 days at 21° C.

*Time and temperature to produce a rooted cutting or liner.*—Summer: 15 to 18 days at 25° C. Winter: 18 to 21 days at 21° C.

*Rooting habit and description.*—Fibrous roots, adventitious roots from cutting base.

Plant:

*General appearance and form.*—Round and compact.

*Growth and branching habit.*—Very good branching.

*Growth rate.*—3 months from rooted plant to a finished product in 12 to 13 cm pots.

*Plant height.*—18 cm.

*Plant width* (*spread*).—30 cm.

Lateral branches:

*Quantity per plant.*—4 main branches that split to 9 secondary branches, (every node splits to 2 to 3 secondary branches).

*Length.*—10 to 12 cm.

*Diameter.*—1.0 to 1.5 cm.

*Internode length.*—5 to 6 cm.

*Strength.*—Strong, very stable.

*Texture.*—Smooth.

*Color.*—Upper surface: Grey-brown group: RHS N199B. Lower surface: Yellow-green group: RHS 146A.

Foliage:

*Arrangement.*—Alternate.

*Overall shape of leaf.*—Lanceolate to ovate.

*Shape at apex.*—Attenuate.

*Shape at base.*—Acuminate.

*Length.*—12 cm.

*Width.*—2.5 cm.

*Margin.*—Ciliate.

*Texture.*—Upper surface: Smooth. Lower surface: Smooth.

*Color of mature* (*developed*) *leaf.*—Upper surface: Green, RHS 137A. Lower surface: Green, RHS 138B.

*Color of immature* (*expanding*) *leaf.*—Upper surface: Green, RHS 137A. Lower surface: Green, RHS 138B.

*Venation pattern.*—Midrib with secondary veins. Pinnate, only lower surface.

*Venation color.*—Upper surface (midrib): Yellow-green, RHS 145C. Lower surface (midrib): Yellow-green, RHS 147C, Secondary veins: Yellow-green RHS 147B.

*Petiole length.*—1 cm.

*Petiole diameter.*—2 mm.

*Petiole color.*—Upper surface: Greyed-red, RHS 181C. Lower surface: Greyed-red, RHS 180C.

Flower description:

*Flower type and habit.*—Single flowers raised above the foliage. The corolla consists of five petals.

*Natural flowering season.*—Flowers at any day length. All year round in a greenhouse environment. Flowering is continuous from spring until fall in an outdoor garden.

*Flowering response.*—12 weeks after planting of rooted cuttings.

*Quantity of flowers.*—The number of blooms is about 25 to 30 flowers per mature plant, 3 months old at any given time.

*Post production longevity.*—Up to six months.

*Fragrance* (*if any*).—None.

Corolla:

*Form.*—Single.

*Shape.*—Round.

*Length.*—7 cm.

*Width.*—7 cm.

*Depth.*—3 mm.
*Color.*—Purple group, RHS N78B.

Buds:
*Rate of opening* (*from showing color to fully open flower*).—10 to 14 days.
*Length* (*showing color, before opening*).—2 cm.
*Diameter.*—At Apex: 0.5 cm. At Base: 1 cm.
*Shape.*—Ovate.
*Color.*—Purple Group, RHS N78B.

Petals:
*Quantity and arrangement per flower.*—5 Petals. The dorsal petal is free. The lateral petals are fused in pairs.
*Banner petal length.*—3.5 cm.
*Lateral and base petal length.*—3.5 cm.
*Banner petal width.*—5 cm.
*Banner lateral and base petals.*—3 cm.
*Overall shape.*—Round.
*Shape at apex.*—Acute.
*Margin.*—Entire.
*Aspect.*—Obcordate.
*Texture.*—Upper surface: Smooth. Lower surface: Smooth.
*Color of opening petals.*—Upper surface: Purple group: RHS N78B. Base color: Red-purple group: RHS 67A. Lower surface: Purple group: RHS N78C. Base color: Red-purple group: RHS 67B.
*Color of fully opened petals.*—Upper surface: Purple group: RHS N78B. Base color: Red-purple group: RHS 67A. Lower surface: Purple group, RHS N78C. Base color: Red-purple group, RHS 67B.

Sepals:
*Quantity per flower.*—2.
*Length.*—About 1.1 cm.
*Width.*—About 5 mm.
*Overall shape.*—Oblong.
*Apex shape.*—Acute.
*Base shape.*—Rounded.
*Margin.*—Entire.
*Color.*—Upper surface: RHS 63B, red-purple group. Lower surface: RHS 63A, red-purple group.

Spur:
*Quantity per flower.*—One.
*Length.*—5.5 cm.
*Diameter.*—At apex: 1 mm. At flower: 3 mm.
*Aspect.*—40° to 45° from peduncle.
*Color of spur.*—Towards base: Red-purple group, RHS 58A. Towards apex: Green group, RHS 142A.

Peduncles:
*Appearance and angle.*—Erect 90° from corolla.
*Length.*—5.5 cm.
*Diameter.*—1 mm.
*Texture.*—Smooth.
*Strength.*—Stable, flexible.
*Color.*—Greyed-purple group, RHS 184B.

Reproductive organs:

Androecium:
*Stamen quantity per flower.*—There are five stamens with introrse anthers that are more or less fused and form a cap over the ovary.
*Filament.*—No filament.
*Anther shape.*—Cap shape.
*Anther length.*—0.3 mm.
*Anther color.*—White group, RHS 155A.
*Pollen amount.*—Abundant amount.
*Pollen color.*—White group, RHS 155D.

Gynoecium:
*Pistil quantity of per flower.*—One.
*Pistil length.*—3 mm.
*Stigma shape.*—Round.
*Stigma color.*—Green-yellow group, RHS 1 D.
*Style length.*—No distinct style.
*Ovary color.*—Yellow-Green group, RHS 144D.

Seeds:
*Quantity.*—About 10 to 15 seeds per fruit.
*Length.*—2 mm.
*Diameter.*—2 mm.
*Shape.*—Ovate.
*Texture.*—Puberulous.
*Color.*—Greyed-orange group, RHS 17A.

Fruit:
*Shape.*—Elliptic.
*Color.*—Green group, RHS 143 C.

Disease/pest resistance: No information is currently available.

Disease/pest susceptibility: No information is currently available.

Low temperature tolerance: Very sensitive to temperatures below 10° C.

I claim:

1. A new and distinct New Guinea *Impatiens* plant named 'Danhardaror', as illustrated and described herein.

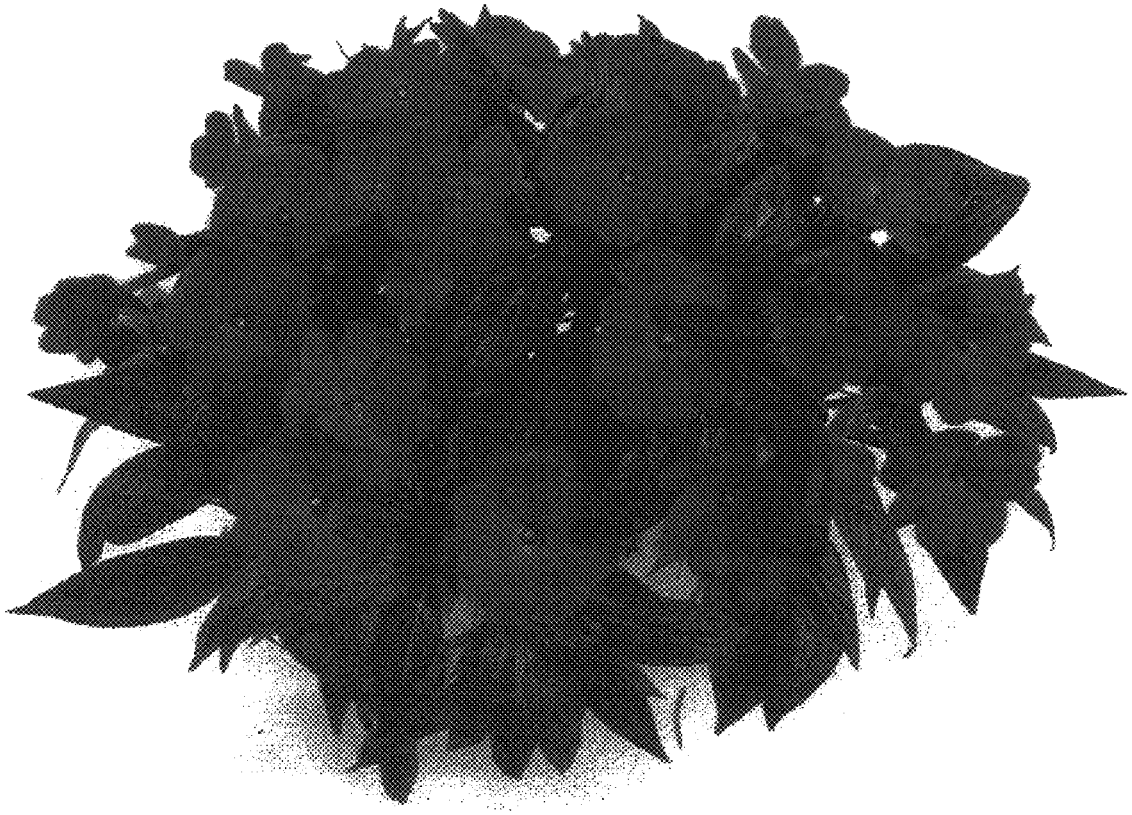

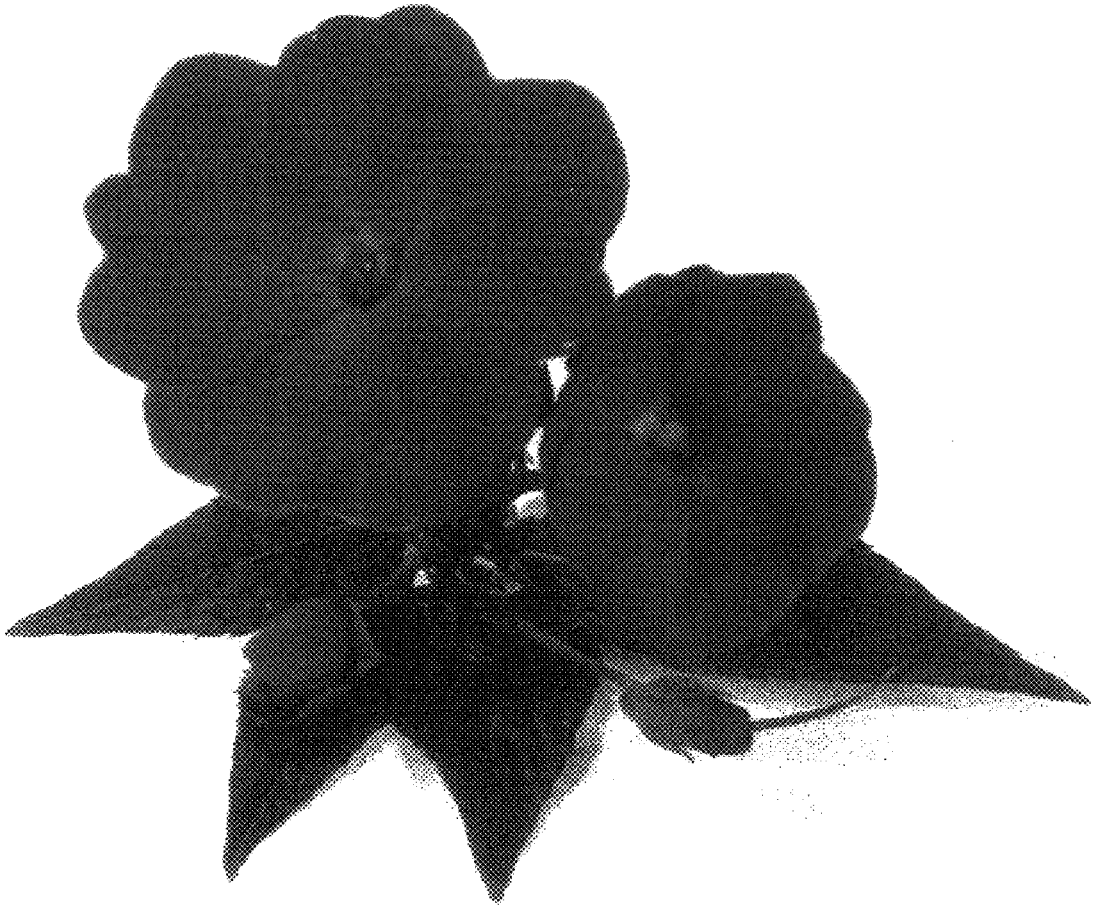

* * * * *